United States Patent
von Yurt et al.

(10) Patent No.: US 8,276,224 B1
(45) Date of Patent: Oct. 2, 2012

(54) BED SHEET WITH INTEGRATED SLEEPING GARMENT

(76) Inventors: Joanna von Yurt, Santa Barbara, CA (US); Jan Marco von Yurt, Santa Barbara, CA (US)

( * ) Notice: Subject to any disclaimer, the term of this patent is extended or adjusted under 35 U.S.C. 154(b) by 0 days.

(21) Appl. No.: 13/439,233

(22) Filed: Apr. 4, 2012

(51) Int. Cl.
*A47G 9/02* (2006.01)
*A41B 13/06* (2006.01)
*A61F 5/37* (2006.01)

(52) U.S. Cl. ............. 5/494; 5/485; 5/497; 5/500; 5/502; 5/655; 2/69.5; 128/873; 128/874

(58) Field of Classification Search ............. 5/494, 495, 5/497, 499, 500, 502, 485, 482, 655, 413 R; 2/114, 83, 69.5, 69; 128/872–874
See application file for complete search history.

(56) References Cited

U.S. PATENT DOCUMENTS

| | | | |
|---|---|---|---|
| 1,403,873 A * | 1/1922 | Scott | 5/494 |
| 1,802,540 A | 4/1931 | Schmidt | |
| 1,964,271 A * | 6/1934 | O'Dwyer | 128/873 |
| 2,140,797 A * | 12/1938 | Hammerman | 2/114 |
| 2,325,097 A * | 7/1943 | Behringer | 128/873 |
| 2,342,069 A | 2/1944 | Wilkinson | |
| 2,376,617 A | 5/1945 | O'Reilley | |
| 2,419,989 A | 5/1947 | Day | |
| 2,451,807 A | 10/1948 | Catizone | |
| 2,481,741 A * | 9/1949 | Graves | 128/873 |
| 2,503,427 A * | 4/1950 | Waterworth | 128/873 |
| 2,702,385 A | 2/1955 | Goldberg | |
| 2,851,703 A | 9/1958 | Greco | |
| 2,888,009 A * | 5/1959 | Taylor | 128/873 |
| 2,940,443 A * | 6/1960 | Baker | 128/874 |
| 3,121,885 A | 2/1964 | Cherry | |
| 3,536,067 A | 10/1970 | Sternagel | |
| 3,845,513 A | 11/1974 | Hubner | |
| 3,872,524 A * | 3/1975 | Hummel | 2/69.5 |
| 3,987,505 A | 10/1976 | Hickey | |
| 4,202,052 A | 5/1980 | Bilanzich | |
| 4,853,996 A * | 8/1989 | Harrigan et al. | 5/494 |
| 5,245,717 A * | 9/1993 | Rudy | 5/507.1 |
| 6,253,380 B1 | 7/2001 | Larsson et al. | |
| 6,301,729 B1 | 10/2001 | Hall | |
| 6,401,248 B1 * | 6/2002 | Christensen | 2/69 |
| 6,631,528 B2 * | 10/2003 | Landry | 5/494 |
| 6,681,422 B2 * | 1/2004 | Landry | 5/494 |
| 6,708,356 B1 | 3/2004 | LaValle | |
| 6,817,048 B1 | 11/2004 | LaRosa | |
| 6,848,131 B1 * | 2/2005 | Landry | 5/494 |
| 6,857,146 B2 * | 2/2005 | Landry | 5/494 |

(Continued)

*Primary Examiner* — Robert G Santos (74) *Attorney, Agent, or Firm* — Knobbe, Martens, Olson and Bear, LLP (57) ABSTRACT

A bed sheet includes a bottom fabric layer sized to extend over the sides of and underneath a mattress. A top fabric layer is generally co-extensive with, and fastened to, the bottom fabric layer and defines a pocket therebetween. A sleeping garment integrated into the top fabric layer has a pair of garment halves removably coupleable to each other via a zipper that zips up into a fastener pocket that covers the zipper when the garment is fully closed. A flap can extend from one half of the garment, over the fastener pocket and fasten to the opposite half of the garment to inhibit the user from unzipping and removing the garment. The garment can hold a lower portion of the user within said pocket, allowing the user to remain warm without the use of a separate blanket, while being able to sit or stand on the mattress.

20 Claims, 7 Drawing Sheets

U.S. PATENT DOCUMENTS

| | | |
|---|---|---|
| D510,792 S | 10/2005 | Vazquez et al. |
| 7,111,344 B2 | 9/2006 | French |
| 7,150,054 B1 | 12/2006 | Byrne et al. |
| D557,880 S | 12/2007 | O'Connor-Cowley |
| 7,370,377 B2 * | 5/2008 | Landry .............. 5/494 |
| 7,584,515 B2 * | 9/2009 | Jones et al. ........ 5/485 |
| 7,673,354 B2 | 3/2010 | Fader |
| 8,020,226 B2 | 9/2011 | Landry |
| 8,056,161 B2 | 11/2011 | Barry |
| 8,191,188 B2 * | 6/2012 | Kaplan et al. ...... 5/485 |
| 2003/0154548 A1 * | 8/2003 | Landry .............. 5/494 |
| 2003/0154549 A1 * | 8/2003 | Landry .............. 5/494 |
| 2004/0019970 A1 * | 2/2004 | Landry .............. 5/494 |
| 2004/0199999 A1 * | 10/2004 | Landry .............. 5/494 |
| 2005/0028278 A1 * | 2/2005 | Landry .............. 5/494 |
| 2005/0210585 A1 * | 9/2005 | French .............. 5/494 |
| 2007/0056098 A1 | 3/2007 | Schmid et al. |
| 2007/0061968 A1 * | 3/2007 | Fader ................ 5/494 |
| 2007/0157384 A1 | 7/2007 | Alexander |
| 2009/0113630 A1 | 5/2009 | Landry |
| 2010/0242173 A1 * | 9/2010 | Landry .............. 5/494 |
| 2010/0275373 A1 * | 11/2010 | Kaplan et al. ...... 5/494 |

\* cited by examiner

BED SHEET WITH INTEGRATED SLEEPING GARMENT

BACKGROUND

1. Field

The present invention is directed to a sleeping garment and more particularly to a bed sheet with an integrated sleeping garment.

2. Description of the Related Art

Bed sheets are commonly known. With respect to infants and toddlers, sleeping garments, such as zip-up pajamas or body suits, sleep sacks and swaddle wraps are known. However, such sleeping garments do not inhibit the infant or toddler from coming near the edges of cribs, which is discouraged as being potentially dangerous, nor do they prevent the infant or toddler from trying to climb out of the crib or bed. Additionally, use of several separate sleeping components, such as bedding sheets, pajamas, blankets, can be expensive. Moreover, use of blankets or separate coverings has been discouraged to prevent possible suffocation of infants.

Accordingly, there is a need for an improved sleeping garment that can allow a user (e.g., infant, toddler, child, adult) to sleep comfortably and securely, while reducing the number of components and addressing some of the deficiencies noted above.

SUMMARY

In accordance with one embodiment, a bed sheet with an integrated sleeping garment is provided. The bed sheet comprises a top fabric layer configured to extend over sides of a mattress to a distal edge on an underside of the mattress, said edge defining a bottom opening. A bottom layer is configured to extend over at least a portion of an upper surface of the mattress, the top layer fastened to the bottom layer so as to define a pocket therebetween. An oval elastic band is attached to the top fabric layer at said distal edge, the elastic band configured to generally maintain one or both of the top and bottom layers generally fitted to the mattress during use of the sheet. A sleeping garment is integrated into the top fabric layer, wherein the top fabric layer defines at least a portion of the garment such that the garment holds a user generally in a center of the mattress when the sheet is fitted to the mattress thereby keeping the user away from edges of the mattress. The garment comprises a pair of garment halves removably coupleable to each other via a fastener along a length of said halves, a pair of arm openings configured to receive a user's arms therethrough, and an opening at the proximal end of the garment configured to extend around the user's neck when in use. The sleeping garment is configured to hold the user such that at least a portion of the user is disposed in the pocket between the top and bottom layers, thereby allowing the user to remain warm without the use of a separate blanket. The garment is also configured to secure the user on the mattress while allowing the user to sit or stand on the mattress without dislodging the bottom layer from the mattress.

In accordance with another embodiment, a bed sheet with an integrated sleeping garment is provided. The bed sheet comprises a bottom fabric layer configured to extend at least over a top surface of a mattress when the sheet is attached to the mattress. A top fabric layer is disposed over the bottom layer, the top layer fastened to the bottom layer so as to define a pocket therebetween. One or both of the top and bottom fabric layers extends over sides of the mattress to a distal edge on an underside of the mattress, said distal edge defining a bottom opening. A sleeping garment is integrated into the top fabric layer, wherein the top fabric layer defines at least a portion of the garment such that the garment holds a user generally in a center of the mattress when the sheet is attached to the mattress, thereby keeping the user away from edges of the mattress. The garment comprises a pair of garment halves removably coupleable to each other via one or more fasteners configured to fasten said two halves of the garment at least within a fastener pocket that covers at least one of the one or more fasteners when the garment is fully closed. The garment further comprises a flap that extends from one half of the garment proximate a neck opening of the garment, over the fastener pocket and is fastened to the opposite half of the garment so that the user is inhibited from accessing at least one of the one or more fasteners, thereby inhibiting the user from removing the garment. The garment also comprises a pair of arm openings configured to receive a user's arms therethrough, and an opening at the proximal end of the garment configured to extend around the user's neck when in use. The sleeping garment is configured to hold the user such that a lower portion of the user is disposed in the pocket between the top and bottom fabric layers, thereby allowing the user to remain warm without the use of a separate blanket. The garment is also configured to secure the user on the mattress while allowing the user to sit or stand on the mattress.

In accordance with still another embodiment, a bed sheet with an integrated sleeping garment is provided. The bed sheet comprises a bottom fabric layer configured to extend over an upper surface of a mattress to which the bed sheet is attached. The bed sheet also comprises a top fabric layer attached to the bottom layer so as to define a pocket therebetween, one or both of the top and bottom fabric layers configured to extend over the sides of the mattress to a distal edge on an underside of the mattress, said edge defining a bottom opening. The bed sheet further comprises a sleeping garment integrated into the top fabric layer, wherein the top fabric layer defines at least a portion of the garment such that the garment holds a user generally in a center of the mattress when the sheet is attached to the mattress, thereby keeping the user away from edges of the mattress. The sleeping garment comprises a pair of garment halves removably coupleable to each other via a zipper that zips up into a fastener pocket that covers the zipper when the garment is fully closed. The garment further comprises a flap that extends from one half of the garment, over the fastener pocket and is fastened to the opposite half of the garment to thereby inhibit the user from accessing the zipper to unzip and remove the garment. The sleeping garment also comprises a pair of arm openings configured to receive a user's arms therethrough, and an opening at the proximal end of the garment configured to extend around the user's neck when in use. The sleeping garment is configured to hold the user such that a lower portion of the user is disposed in the pocket between the top and bottom fabric layers, thereby allowing the user to remain warm without the use of a separate blanket, the garment also configured to secure the user on the mattress while allowing the user to sit or stand on the mattress.

BRIEF DESCRIPTION

DETAILED DESCRIPTION

As used herein, a "mattress" is meant to encompass any cushioned sleeping pad, where the sleeping pad can be filled with resilient material, such as cotton, feathers, foam rubber, or can have one or more springs, as in a common mattress of a bed, or can be filled with water or air. As used herein, a "mattress" is meant to encompass different sized mattresses, such as crib size, twin size, full size, queen size and king size, as well as mattresses of different thickness, such as bassinet pads, crib mattresses and up to king size mattresses.

FIGS. 1-6 show one embodiment of a bed sheet 100. The bed sheet 100 can have a top layer 10 generally sized to extend along a length L and width W of a mattress 200. The top layer 10 can at least partially define a sleeping garment 60, which is further described below.

The top layer 10 is attached to a bottom layer 20 so as to define a pocket or cavity 30 therebetween into which a wearer of the sleeping garment can at least partially extend. In the illustrated embodiment, the top layer 10 is generally co-extensive with the bottom layer 20. However, in other embodiments, the bottom layer 20 can extend over a larger area than the top layer 10. In the illustrated embodiment, the top layer 10 is sewn to the bottom layer 20 along at least a portion of the periphery 12 of the top layer 10. In one embodiment, the periphery 12 of the top layer 10 is side to substantially correspond to the periphery of a top surface 210 of the mattress 200 on which the top layer 10 rests. In another embodiment, the periphery 12 of the top layer 10 is larger than the periphery that defines the top surface 210 of the mattress 200 so that the top layer 10 extends past the edges of said top surface and onto a side surface 220 of said mattress 200.

With continued reference to FIGS. 1-6, the bed sheet 100 can also include a substantially generally water-resistant layer or water proof layer 40 disposed below the bottom layer 20, so that the waterproof layer 40 is adjacent and in contact with the mattress 200 when the sheet 100 is placed on the mattress 200, and so the bottom layer 20 is disposed between the waterproof layer 40 and the top layer 10. In one embodiment, the top layer 10 is generally co-extensive with the bottom layer 20 and the waterproof layer 40, and the three layers 10, 20, 40 are sewn together along at least a portion of the periphery 12 of the top layer. In one embodiment, the waterproof layer 40 extends along an area smaller than the top layer 10, where the waterproof layer 40 extends along substantially the top surface 210 of the mattress 200. In another embodiment, the waterproof layer 40 can extends along the same area as the top layer 10, and can extend to the sides 220 or underside surface 230 of the mattress 200. Advantageously, the waterproof layer 40 can at least partially stick or adhere to the mattress 200 during use (e.g., due to the affinity between the mattress material and material of the waterproof layer 40), which advantageously helps to maintain the bed sheet 100 in place on the mattress 200 and inhibits dislodgement of the sheet 100 during use (e.g., due to the user moving around, sitting up or standing up). In another embodiment the water proof layer 40 can be excluded from the bed sheet 100. In one embodiment, where the water proof layer 40 is excluded from the bed sheet 100, the bottom layer 20 can be water resistant or water proof.

In one embodiment, the top layer 10 can be made of a breathable fabric, such as cotton. However, in other embodiments, the In one embodiment, the top layer 10 can be of a stretchable material, such as 100% jersey cotton stretch material, which advantageously allows the user to comfortably move while having the sleeping garment 60 on. However, in other embodiments, the top layer 10 can be made of other suitable fabrics or textiles, including those made from natural or synthetic fibers (e.g., polyester). In one embodiment, the bottom layer 20 can be made of fabric. For example, in one embodiment, the bottom layer 20 can be made of 100% cotton flannel. However, in other embodiments, the top layer 10 can be made of other suitable fabrics or textiles, including those made from natural or synthetic fibers (e.g., polyester, terry-cloth, bamboo). In one embodiment, the waterproof layer 40 can be made of a polymer material, such as plastic or vinyl coated polyester. However, in other embodiments, the waterproof layer 40 can be made of other suitable materials, such as a plastic material (e.g., natural, synthetic or semi-synthetic plastic material).

The bed sheet 100 can have a side portion 50 configured to extend from the top layer 10, along the sides 220 of the mattress 200 and to an underside 230 of the mattress 200. In one embodiment, the side portion 50 and top layer 10 are one piece. In another embodiment, the side portion 50 and top layer 10 are separate pieces that are sewn together at said periphery 12. In one embodiment, the side portion 50 can be made of the same material as the top layer 10. In another embodiment, the side portion 50 can be made of a different material than the top layer 10.

As noted above, the side portion 50 can extend to the underside 230 of the mattress 200 and define an edge 52. A resilient (e.g., elastic) band 54 can be attached to at least a portion of said edge 52 or be integrated in the edge 52 (e.g., the side portion 50 can overlap the band 54 at said edge 52 so as to enclose the band 54). In the illustrated embodiment, the elastic band 54 can extend along the entire edge 52. In one embodiment, the band 54 can have a generally oval shape when in the relaxed or unstretched condition. Advantageously, the band 54 substantially maintains the sheet 100 in place on the mattress 200 and inhibits the sheet 100 from dislodging or coming off the mattress 200 during use of the sheet 100 by a user, as further discussed below. In one embodiment, the band 54 has a thickness 54t of about three inches. However, in other embodiments, the thickness 54t can be less than or greater than three inches.

Figure 1:
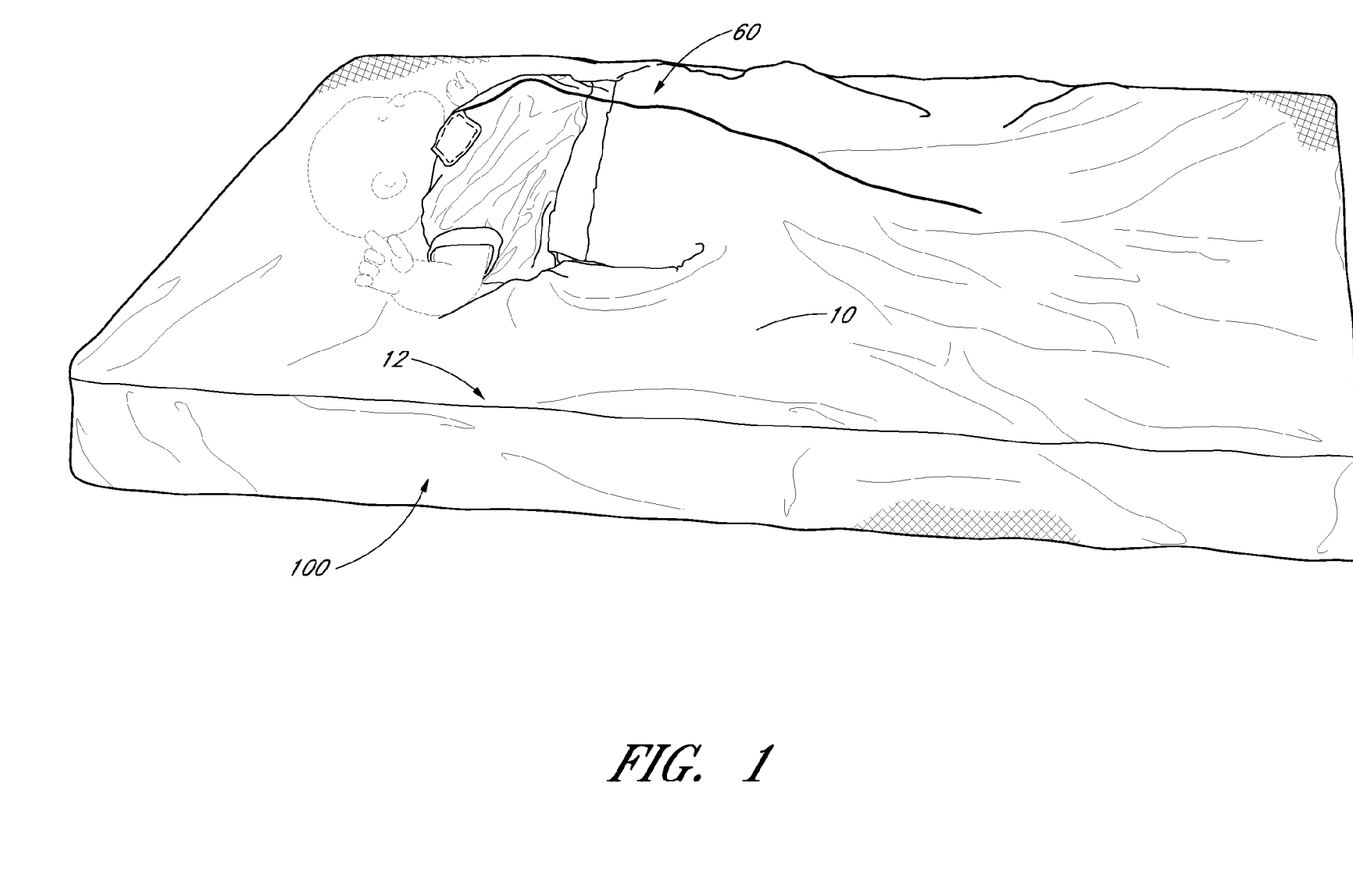
FIG. 1 is a schematic perspective top view of one embodiment of a bed sheet with an integrated sleeping garment, with a user wearing the garment and laying down.
Figure 2:
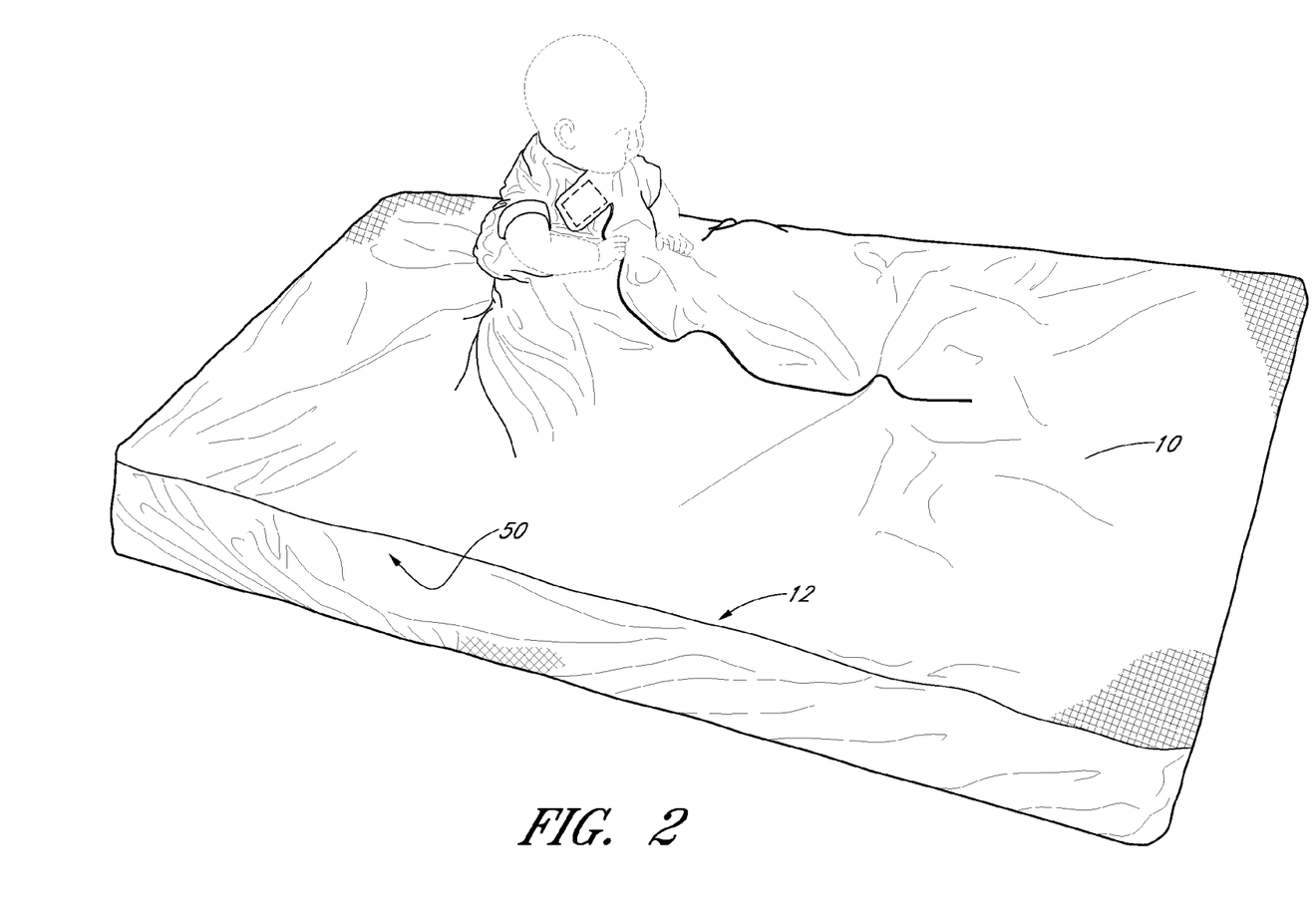
FIG. 2 is a schematic perspective top view of the bed sheet of FIG. 1, with the user wearing the garment and sitting up.
Figure 3:
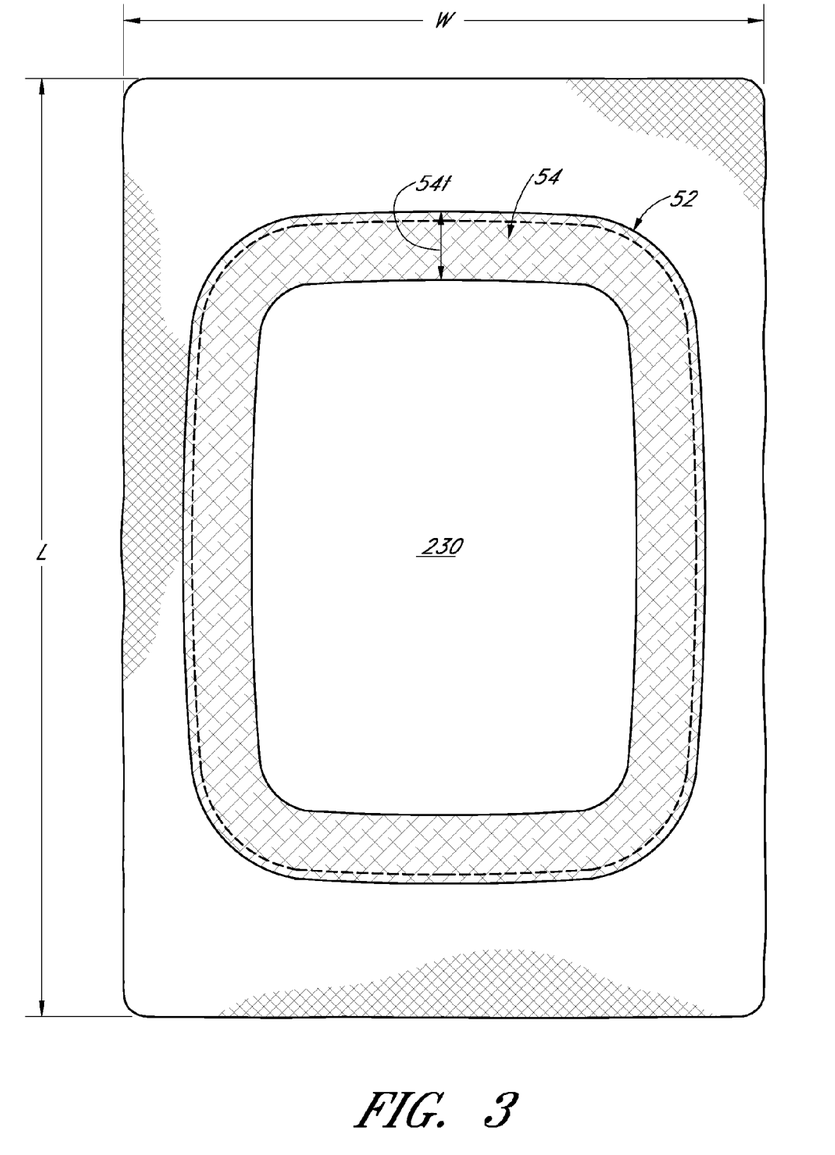
FIG. 3 is a schematic bottom view of the bed sheet of FIG. 1 disposed over a mattress
Figure 4:
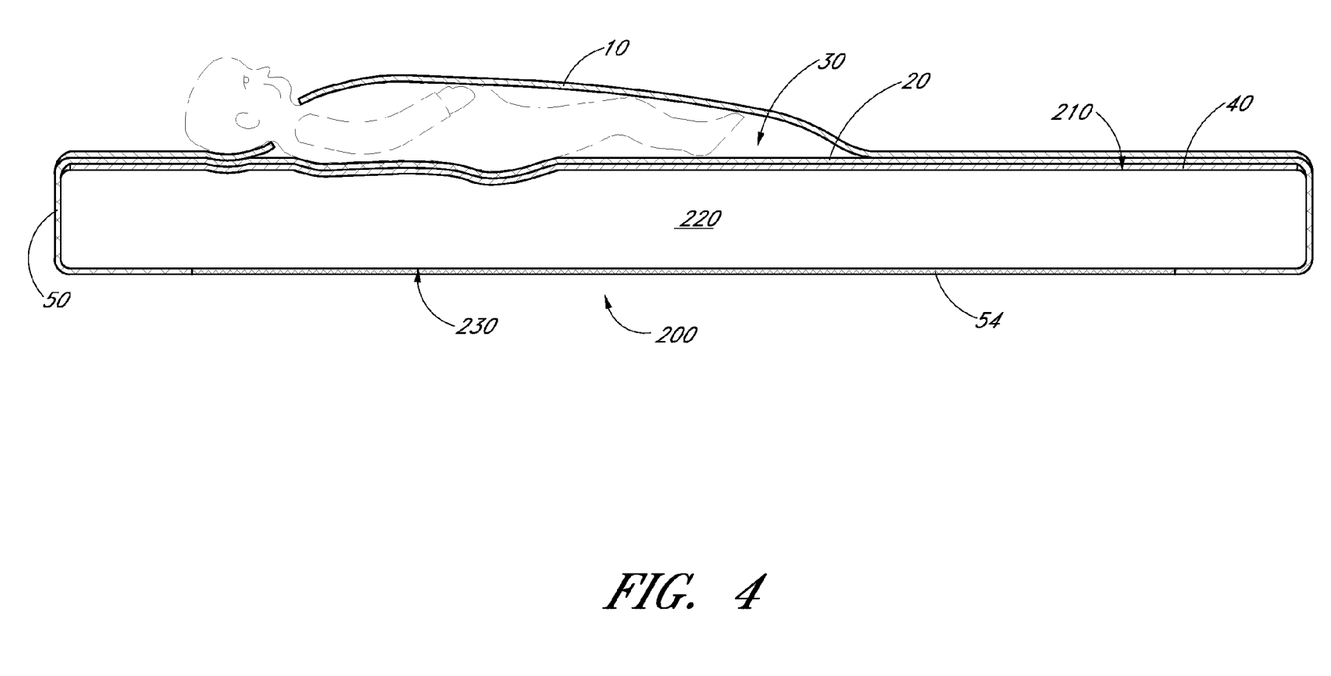
FIG. 4 is a schematic cross-sectional side view of the bed sheet of FIG. 1 with the user lying down.
Figure 5:
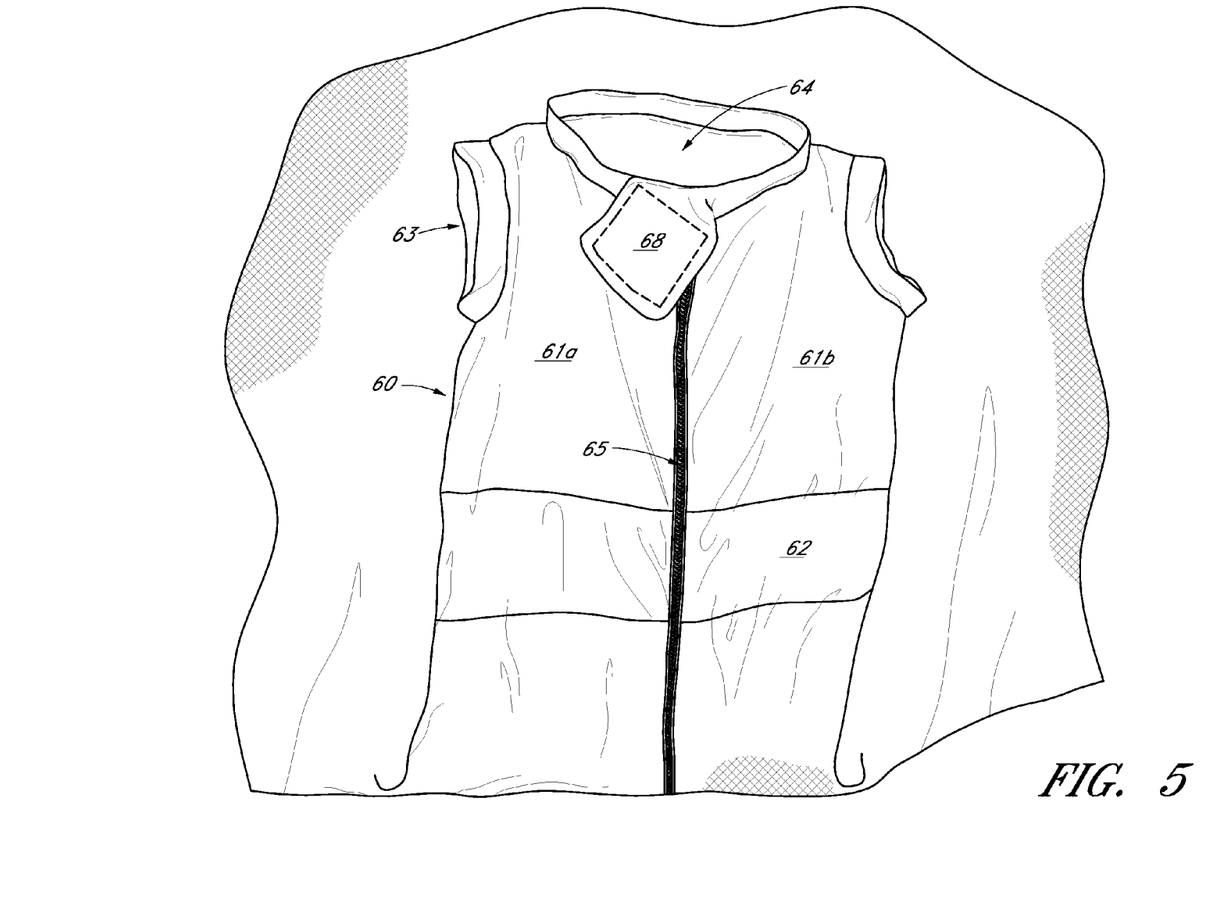
FIG. 5 is a schematic front view of a portion of the sleeping garment of the bed sheet of FIG. 1

With continued reference to FIGS. 1-6, the sleeping garment 60 can be integrated into the bed sheet 100 so that the garment 60 and top layer 10 are a single piece. In the illustrated embodiment, as best shown in FIG. 5, the sleeping garment 60 can be a vest with two halves 61a, 61b that generally extend from the user's waist up to his or her neck. The sleeping garment 60 can have a waist band 62, which can be of a resilient and stretchable material, a pair of arm openings 63 (e.g., proximate the location of the shoulders of the user) through which the user's arms can extend, and a neck opening 64 through which the user's neck extends when the user is wearing the garment 60. In another embodiment, the sleeping garment can have sleeves (e.g., short or long sleeves) that extend from the arm openings 63 (e.g., from a seam between the sleeping garment and sleeves that defines the arm openings) to a distal end of the sleeves. In one embodiment, such sleeves can be removably attachable to the halves 61a, 61b of the garment 60 proximate said openings 63. In another embodiment, such sleeves can be integrated into the halves 61a, 61b of the garment 60 (e.g., via a seam proximate said openings 63). In one embodiment, where the sleeves are long sleeves, mittens can be integrated into the sleeves at the distal ends thereof so that the user's arms are completely enclosed.

The halves 61a, 61b of the sleeping garment 60 can be removably attachable to each other by one or more fasteners 65 along at least the length of the sleeping garment 60, where the one or more fasteners 65 allow access to an interior of the sleeping garment 60 to allow placement of the user within the garment 60. In the illustrated embodiment, the one or more fasteners 65 are located along a front side of the sleeping garment 60. However, in another embodiment, the one or more fasteners 65 can be located along a rear side of the sleeping garment 60. In still another embodiment, the one or more fasteners 65 can be located along the front side and rear side of the sleeping garment 60. In another embodiment, the one or more fasteners 65 can be located along a right aide or left side of the sleeping garment 60. In the illustrated embodiment, the fastener 65 is a zipper that can be operated to close the garment 60 from its distal end to a position proximate the neck opening 64. In one embodiment, the zipper can be about 24 inches long, though other lengths are possible. However, in other embodiments, the one or more fasteners 65 can be other suitable mechanisms for attaching the two halves 61a, 61b of the sleeping garment 60. For example, in some embodiments, the one or more fasteners 65 can include hoop and loop fasteners, such as VELCRO® or APLIX™. In other embodiments, the fasteners 65 can include buttons on one of the halves 61, 61b that can be inserted into button holes on the other of the halves 61a, 61b. In still another embodiment, the fasteners 65 can be snaps arranged along the length of the halves 61a, 61b.

Figure 6:
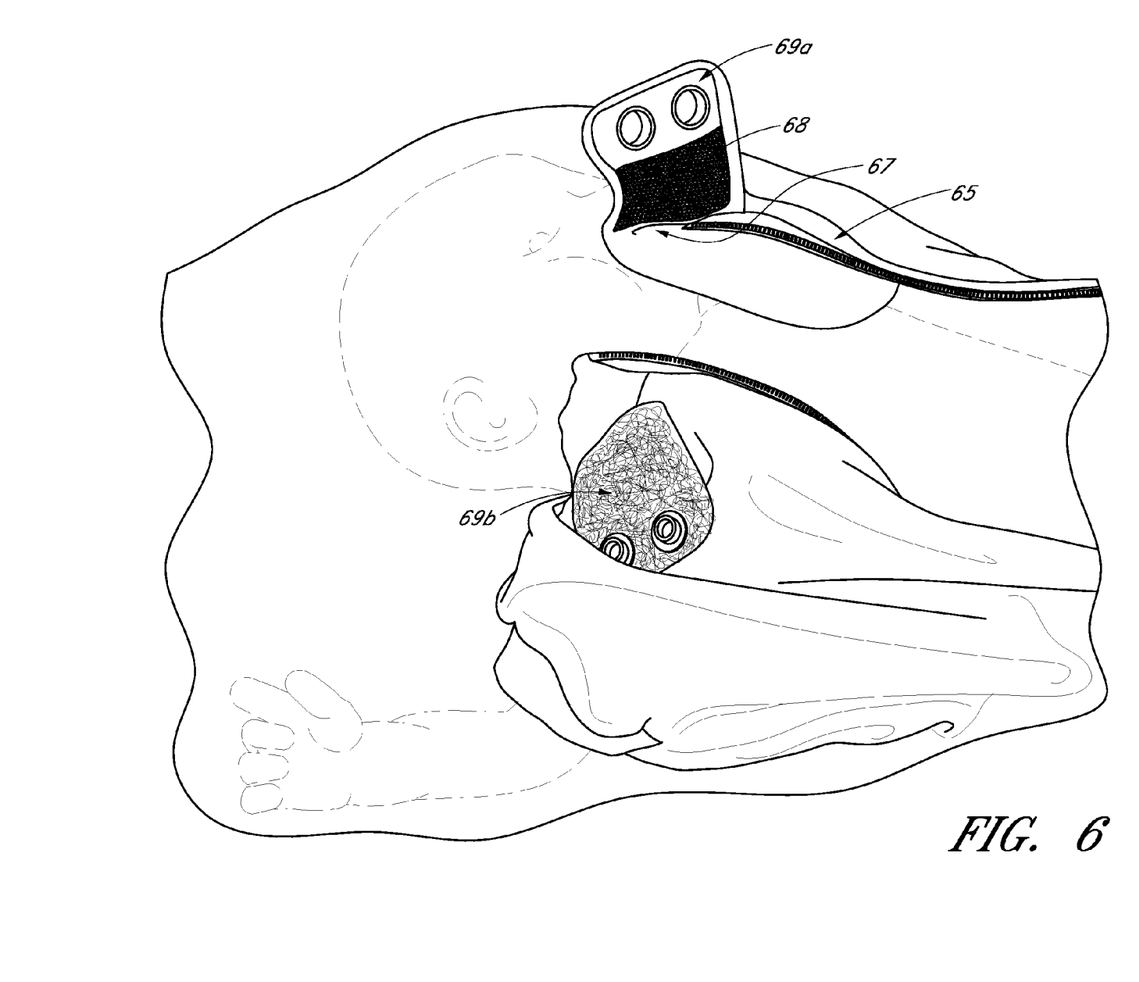
FIG. 6 is a schematic top perspective view of a fastening mechanism of the integrated garment in FIG. 1.

With continued reference to FIGS. 5-6, at least a portion of the fastener 65 preferably extends in a pocket 67 defined by a fold 68 that covers the proximal end of the garment 60 near the neck opening 64 when the fastener 65 is actuated to close the sleeping garment 60. In the illustrated embodiment, where the fastener 65 is a zipper, the zipper can extend into the pocket 67 so as to be hidden from view. The fold 68 can include a flap 68a that folds over the fastener 65 to enclose the fastener 65 in the pocket 67. The flap 68a can include one or more flap fasteners 69a to removably couple the flap to one of the halves 61a, 61b of the garment 60. In the illustrated embodiment, the flap fasteners 69a can include a hoop and loop fastener (e.g., VELCRO®, APLIX™) and one or more snaps (e.g., two snaps). However, in other embodiments, the flap fasteners 69a can be other suitable mechanism. For example, in other embodiments, the flap fasteners 69a can include buttons, only snaps, only a hoop and loop fastener, or a combination of any of these.

Advantageously, the pocket 67 obstructs the fastener 65 so that the fastener 65 does not rub up against the chin of the user (e.g., infant, toddler) and thereby harm or irritate the skin of the user. Additionally, the pocket 67 and flap 68a maintain the fastener 65 hidden to inhibit the user from placing the fastener in his or her mouth and accidentally ingesting the fastener 65. Further, the pocket 67 and flap 68a advantageously maintain the fastener 65 hidden so as to inhibit the user from accessing the fastener 65 to unfasten and remove the sleeping garment 60. Accordingly, the pocket 67 and flap 68a facilitate the securement of the user with the garment 60. In one embodiment, where the user is an infant or toddler and the bed sheet 100 is placed on a crib mattress, the pocket 67 and flap 68a can advantageously inhibit the user from accessing and operating the fastener 65 to remove the sleeping garment 60 and exit the crib.

In one embodiment, at least a portion of the sleeping garment 60 can be made of the same material as the top layer 10. In another embodiment, the sleeping garment 60 can be made of a different material than the top layer 10. In the illustrated embodiment, one or more of the waist band 62, arm holes or openings 63, neck opening 64 and fold 68 can be made of, or lined with a stretchable fabric, such as Debutante satin stretch fabric (e.g., made of 94% polyester and 6% LYCRA®). Additionally, the fastener 65 (e.g., zipper) can be lined with a trim made of stretchable material, such as stretch elastic piping. Such stretchable material allows the sleeping garment 60 to more securely fit to the user for a customized fit. In one embodiment, the waist band 62 is sewn to the garment 60 with the grain generally vertical, which allows for an additional extension or stretch of the garment 60 that allows the user to stand up while wearing the garment 60 without pulling or dislodging the sheet 100 from the mattress 200. In one embodiment, the sleeping garment 60 can have one or more fasteners on a rear surface of the garment 60 that can removably attach to one or more fasteners on the top layer 10 of the bed sheet 100 to help encourage the user to sleep on his or her back while in the garment 60.

In one embodiment, a material tab can be attached to the bed sheet 100 approximately an arm's length from the user. The material tab, in one embodiment, can have one or more snap ends and could be used to attach security items for use by the user (e.g., silkie, security blanket) with another end of the snap.

Figure 7:
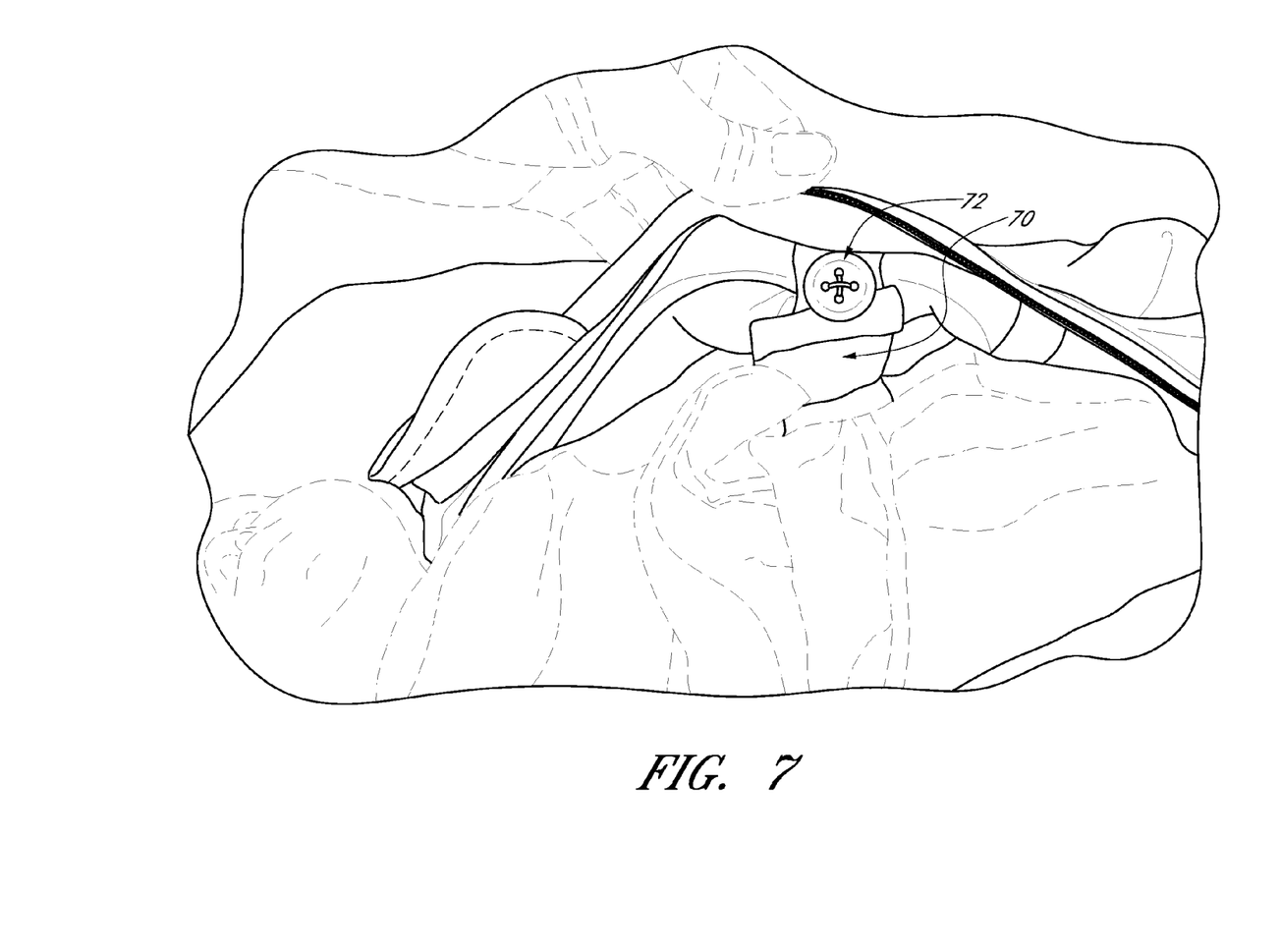
FIG. 7 is a schematic top view of another embodiment of a bed sheet with a sleeping garment.

FIG. 7 shows another embodiment of a bed sheet 100'. The bed sheet 100' is similar to the bed sheet 100 described above and can have the same components as the bed sheet 100, except as noted below. Thus, the reference numerals used to designate the various components of the bed sheet 100' are identical to those used for identifying the corresponding components of the bed sheet 100 in FIGS. 1-6, except that a "'" has been added to the reference numerals. Unless noted below, the description of the components of the bed sheet 100' is the same as the description of the corresponding components of the bed sheet 100 provided above.

As shown in FIG. 7, the sleeping garment 60' can have an adjustable waist band 70' on an inner surface of the garment 60'. In the illustrated embodiment, the waist band 70' is an elastic waist band that extends from one edge of one half 61a' of the garment 60' to the opposite edge of the other half 61b' of the garment 60'. In another embodiment, the garment 60' can have two waist bands 70', one extending from the back of the garment 60' to the edge of one half 61a' of the garment 60', and the other extending from the back of the garment 60' to the edge of the other half 61b' of the garment 60'. The waist band 70' can have multiple button holes, where the waist band 70' can be stretched to a desired length and coupled to a button 72' at a desired button hole (not shown) of the waist band 70' to maintain the desired length. The button 72' can be proximate the edge of the garment halves 61a', 61b'. The waist band 70' can advantageously allow the waist of the sleeping garment 60' to be adjusted to securely accommodate users of varying waist sizes.

Advantageously, the bed sheet 100 provides a one-piece sheet that can be placed on the mattress 200 without the need to use sheets or blankets to cover the user, thereby providing a simplified sleeping system for users. In particular, where users are infants or toddlers, parents can use the bed sheet 200, without additional sheets or blankets, to keep the infant/toddler warm, comforted and secure while sleeping, thereby inhibiting potential risks from the use of such loose blankets. Additionally, the bed sheet 100 advantageously encourages the user to sleep on his or her back (e.g., due to the location of the sleeping garment 60 generally in the center of the mattress 200 when the sheet 100 is placed on the mattress 200), which can reduce the risk of sudden infant death syndrome (SIDS). Further, as the bed sheet 100 is securely held on the mattress 200 to inhibit dislodgement of the bed sheet 100 from the mattress 200 by the user, the bed sheet 100 encourages the user to sleep on his or her back and inhibits the user from sleeping in another position. Moreover, the location of the sleeping garment 60 on the bed sheet 100, such that the infant/toddler is generally centrally positioned on the mattress 200 advantageously securely maintains the infant/toddler away from the edges of the crib, thereby reducing the potential for injuries from the infant/toddler getting close to the crib edges. Further, the bed sheet 100 and sleeping garment 60 advantageously allow the infant/toddler to sit up and/or stand up while wearing the garment 60, while inhibiting the user from climbing out of the crib, thereby reducing the risk of injury from said infant/toddler attempting to climb out of the crib. Accordingly, the bed sheet 100, provides an improved and simplified sleeping system for users (e.g., infants and toddlers) that provides warmth while sleeping and securely holds them, while allowing some movement, while saving cost from avoiding the purchase of multiple sheets and/or blankets and pajamas. Additionally, the bed sheet 100 is a fitted sheet so that when placed on the mattress 200, the top layer 10 is substantially fitted and planar along substantially the entire area (e.g., entire length and width) of the top surface of the mattress 200. Therefore the bed sheet 100 advantageously prevents the presence of loose portions of the top layer 10 material, which might accidentally cover the user's head and pose a hazard (e.g., choking or suffocation hazard) when the user is in a reclined position (e.g., laying down) on the bed.

Though some embodiments above describe the bed sheet 100 as used with infants and toddlers, one of ordinary skill in the art will recognize that the bed sheet 100 can be used with users of all ages and sizes, and with mattresses 200 of all sizes. In one embodiment, the bed sheet 100 can be sized to fit on a twin mattress for use by young children that are ready to transition from a crib to a bed. In such an embodiment, the bed sheet 100 can advantageously hold the child securely on the mattress 200 and prevent the child from falling out of the bed while learning to sleep in a larger bed (e.g., and adult bed).

In another embodiment, the bed sheet 100 can have a swaddle portion (not shown). In one embodiment, the swaddle portion can be integrated into the sleeping garment 60. In another embodiment, the swaddle portion can be removably attachable to the sleeping garment 60. For example, the swaddle portion can have a belt that attaches to a rear side of the sleeping garment 60 (e.g., via a hoop and loop attachment mechanism, snaps, buttons, etc.). The ends of the belt can attach to a swaddle wrap member, each of which can be wrapped around the user's arms from one side of the sleeping garment 60 to the other side of the sleeping garment 60. In one embodiment, the swaddle wrap members can resemble wings that extend from the sides of the sleeping garment 60 and can wrap around the opposite side of the garment 60 to generally immobilize the user's arms. The swaddle wrap members can be removably attached to the sleeping garment 60 or top layer 10 (e.g., via a hoop and loop attachment mechanism, snaps, buttons, etc.). The swaddle portion can advantageously comfortably and securely hold the user, as well as aid the user to sleep on his or her back. In particular, where the user is an infant, the swaddle portion can provide a secure garment that can make the infant feel like he or she is being embraced. In one embodiment, where the swaddle portion is removably attached to the bed sheet 100, the swaddle portion can be removed for washing or when the user, such as a child, has outgrown its use.

Although these inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above

What is claimed is:

1. A bed sheet with an integrated sleeping garment, comprising:
   a top fabric layer configured to extend over sides of a mattress to a distal edge on an underside of the mattress, said distal edge defining a bottom opening;
   a bottom layer configured to extend over at least a portion of an upper surface of the mattress, the top layer fastened to the bottom layer so as to define a pocket therebetween;
   an oval elastic band attached to the top fabric layer at said distal edge, the elastic band configured to generally maintain one or both of the top and bottom layers generally fitted to the mattress during use of the sheet; and
   a sleeping garment integrated into the top fabric layer wherein the top fabric layer defines at least a portion of the garment such that the garment holds a user generally in a center of the mattress when the sheet is fitted to the mattress thereby keeping the user away from edges of the mattress, the garment comprising
      a pair of garment halves removably coupleable to each other via a fastener along a length of said halves,
      a pair of arm openings configured to receive a user's arms therethrough,
      an opening at the proximal end of the garment configured to extend around the user's neck when in use,
   wherein the sleeping garment is configured to hold the user such that at least a portion of the user is disposed in the pocket between the top and bottom layers, thereby allowing the user to remain warm without the use of a separate blanket, the garment also configured to secure the user on the mattress while allowing the user to sit or stand on the mattress without dislodging the bottom layer from the mattress.

2. The sheet of claim 1, wherein the bottom layer comprises a waterproof layer configured to be disposed adjacent the mattress and a liner fabric layer disposed over the waterproof layer such that the waterproof layer is disposed between the liner fabric layer and the mattress.

3. The sheet of claim 2, wherein the top fabric layer comprises cotton, the liner fabric layer comprises flannel and the waterproof layer comprises vinyl coated polyester.

4. The sheet of claim 1, wherein the fastener comprises a zipper, wherein the zipper zips up into a fastener pocket that covers the zipper when the garment is fully closed, the garment further comprising a flap that extends from one half of the garment, over the fastener pocket and fastened to the opposite half of the garment so that the user is inhibited from accessing the zipper thereby inhibiting the user from unzipping and removing the garment.

5. The sheet of claim 1, wherein the garment further comprises a pair of sleeves attached to the arm openings and a waist band generally located at about a waist of the user, the waist band being adjustable to adjust it size to the particular size of the user, such that the garment is configured to fit a plurality of users of different waist sizes.

6. The sheet of claim 1, wherein the mattress is a crib mattress and the garment is configured to fit an infant or toddler.

7. The sheet of claim 1, wherein the elastic band has a width of about three inches when in an unstretched state.

8. A bed sheet with an integrated sleeping garment, comprising:
   a bottom fabric layer configured to extend at least over a top surface of a mattress when the sheet is attached to the mattress;
   a top fabric layer disposed over the bottom layer, the top layer fastened to the bottom layer so as to define a pocket therebetween, where one or both of the top and bottom fabric layers extends over sides of the mattress to a distal edge on an underside of the mattress, said distal edge defining a bottom opening; and
   a sleeping garment integrated into the top fabric layer wherein the top fabric layer defines at least a portion of the garment such that the garment holds a user generally in a center of the mattress when the sheet is attached to the mattress thereby keeping the user away from edges of the mattress, the garment comprising
      a pair of garment halves removably coupleable to each other via one or more fasteners configured to fasten said two halves of the garment at least within a fastener pocket that covers at least one of the one or more fasteners when the garment is fully closed, the garment further comprising a flap that extends from one half of the garment proximate a neck opening of the garment, over the fastener pocket and fastened to the opposite half of the garment so that the user is inhibited from accessing at least one of the one or more fasteners thereby inhibiting the user from removing the garment,
      a pair of arm openings configured to receive a user's arms therethrough,
      an opening at the proximal end of the garment configured to extend around the user's neck when in use,
   wherein the sleeping garment is configured to hold the user such that a lower portion of the user is disposed in the pocket between the top and bottom fabric layers, thereby allowing the user to remain warm without the use of a separate blanket, the garment also configured to secure the user on the mattress while allowing the user to sit or stand on the mattress.

9. The sheet of claim 8, further comprising a waterproof layer disposed between the bottom fabric layer and the mattress.

10. The sheet of claim 9, wherein the top fabric layer comprises cotton, the bottom fabric layer comprises flannel and the waterproof layer comprises vinyl coated polyester.

11. The sheet of claim 8, wherein the one or more fasteners comprises a zipper.

12. The sheet of claim 8, further comprising a pair of sleeves attached to the arm openings and an elastic band attached to one or both of the top and bottom fabric layers at said distal edge, the elastic band configured to generally maintain at least the bottom fabric layer generally fitted about the mattress during use of the sheet while inhibiting dislodgement of the bottom fabric layer from beneath the mattress.

13. The sheet of claim 12, wherein the elastic band has a generally oval shape and a width of about three inches when in an unstretched state.

14. The sheet of claim 8, wherein the garment further comprises a waist band generally located at about a waist of the user, the waist band being adjustable to adjust it size to the particular size of the user, such that the garment is configured to fit a plurality of users of different waist sizes.

15. The sheet of claim 8, wherein the mattress is a crib mattress and the garment is configured to fit an infant or toddler.

16. The sheet of claim 8, wherein the top fabric layer comprises an attachment portion disposed proximate a waist portion of the garment, the attachment portion configured to removably couple to one or more security items for use by the user when in said garment.

17. A bed sheet with an integrated sleeping garment, comprising:
   a bottom fabric layer configured to extend over an upper surface of a mattress to which the bed sheet is attached;
   a top fabric layer attached to the bottom layer so as to define a pocket therebetween, one or both of the top and bottom fabric layers configured to extend over the sides of the mattress to a distal edge on an underside of the mattress, said edge defining a bottom opening; and
   a sleeping garment integrated into the top fabric layer wherein the top fabric layer defines at least a portion of the garment such that the garment holds a user generally in a center of the mattress when the sheet is attached to the mattress thereby keeping the user away from edges of the mattress, the garment comprising
      a pair of garment halves removably coupleable to each other via a zipper that zips up into a fastener pocket that covers the zipper, when the garment is fully closed, the garment further comprising a flap that extends from one half of the garment, over the fastener pocket and fastened to the opposite half of the garment to thereby inhibit the user from accessing the zipper to unzip and remove the garment,
      a pair of arm openings configured to receive a user's arms therethrough,
      an opening at the proximal end of the garment configured to extend around the user's neck when in use,
   wherein the sleeping garment is configured to hold the user such that a lower portion of the user is disposed in the pocket between the top and bottom fabric layers, thereby allowing the user to remain warm without the use of a separate blanket, the garment also configured to secure the user on the mattress while allowing the user to sit or stand on the mattress.

18. The sheet of claim 17, further comprising a waterproof layer disposed between the bottom fabric layer and the mattress.

19. The sheet of claim 17, further comprising an oval elastic band attached to one or both of the top and bottom fabric layers at said distal edge, the elastic band configured to generally maintain at least the bottom fabric layer generally fitted about the mattress during use of the sheet while inhibiting dislodgement of the bottom fabric layer from beneath the mattress.

20. The sheet of claim 17, further comprising a pair of sleeves attached to the arm openings.

* * * * *